United States Patent [19]
Ionescu et al.

[11] 4,084,268
[45] Apr. 18, 1978

[54] PROSTHETIC TISSUE HEART VALVE

[75] Inventors: Marian I. Ionescu, Leeds, England; Bruce E. Fettel, Diamond Bar, Calif.

[73] Assignee: Shiley Laboratories, Incorporated, Santa Ana, Calif.

[21] Appl. No.: 679,406

[22] Filed: Apr. 22, 1976

[51] Int. Cl.² .............................................. A61F 1/22
[52] U.S. Cl. ......................................................... 3/1.5
[58] Field of Search ........................................ 3/1.5, 1

[56] References Cited

U.S. PATENT DOCUMENTS

| 3,714,671 | 2/1973 | Edwards | 3/1.5 |
| 3,755,823 | 9/1973 | Hancock | 3/1.5 |
| 3,983,581 | 10/1976 | Angell et al. | 3/1.5 |
| 3,996,623 | 12/1976 | Kaster | 3/1.5 |

FOREIGN PATENT DOCUMENTS

| 1,264,472 | 2/1972 | United Kingdom | 3/1.5 |

OTHER PUBLICATIONS

"Frame-Mounted Tissue Heart Valves: Technique of Construction" by Ivan T. Bartek et al., Thorax, (1974), 29, pp. 51–55.

"Heart Valve Replacement With Autologous Fascia Lata Using the Ionescu Technique" by A. S. Trimble et al., The Journal of Thoracic & Cardiovascular Surgery, vol. 61, No. 3, Mar. 1971, pp. 385–392.

"Heart-Valve Replacement With Autologous Fascia Lata," by M. I. Ionescu, The Lancet, Aug. 6, 1969, pp. 335–338.

Primary Examiner—Ronald L. Frinks
Attorney, Agent, or Firm—Knobbe, Martens, Olson, Hubbard & Bear

[57] ABSTRACT

A tissue heart valve has a cloth-covered stent which provides several layers of padding over the stent edges and an integral sewing ring while maximizing the internal valve diameter for a given size heart annulus. No edges of the cloth are exposed. A continuation of the pledget covers all knots of the stitches connecting the tissue to the stent.

14 Claims, 9 Drawing Figures

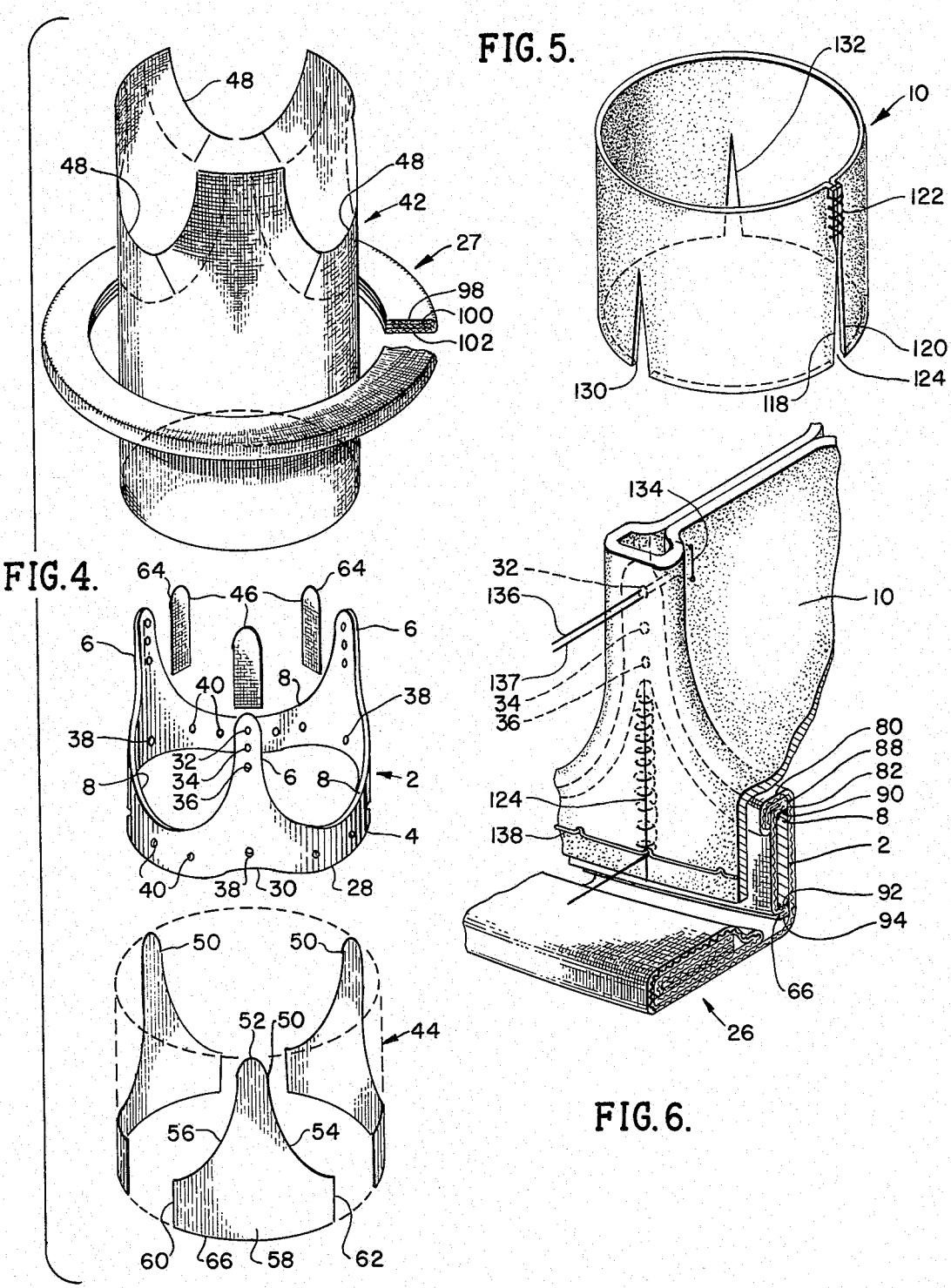

PROSTHETIC TISSUE HEART VALVE

BACKGROUND

This invention relates to frame mounted, prosthetic tissue heart valves, and particularly to improvements in the construction of such valves.

Frame-mounted fascia lata heart valves were used clinically by Dr. Marian I. Ionescu and Dr. D. N. Ross in 1969. Since that time hundreds of tissue valves made of autologous or homologous fascia lata, dura mater, or of heterologous pericardium have been implanted. A construction of bovine pericardial valves is reported in *Frame-mounted Tissue Heart Valves: Technique of Construction*, Bartels, Holden and Ionescu, Thorax (1974) 29, 51. As reported in that article, an important factor on which the long-term function of these valves depends is their construction before insertion. This invention is an improved construction over that described in the cited article.

SUMMARY OF INVENTION

This invention is directed to an improved construction principally in the cloth covering for the valve frame or stent by which raw fabric or tissue edges are not exposed to the blood stream, particularly at the valve inlet, added protection is obtained against the frame or stitches tearing through the covering cloth, risk of the sewing ring separating from the valve is eliminated, the stitches attaching the tissue to the stent are covered by cloth, and the thickness of material at the annulus is reduced to increase the ratio of valve internal diameter to external valve diameter, and therefore to internal diameter of the heart annulus receiving the valve.

Accordingly, this invention provides a prosthetic tissue heart valve in which a continuation of the pledget covers the knots of the threads used to stitch the tissue to the stent. This invention also provides a construction wherein the interior fabric cover is integral with the sewing ring or cuff. Further in accordance with this invention several layers of padding are provided along the edges of the stent where tearing is most likely and cushioning is desirable, yet only three layers of cloth add to the thickness of the stent at the bottom portion which fits in the heart annulus. Moreover, this invention provides a novel construction wherein no edges of the cloth fabric covering the stent are exposed to the bloodstream.

DESCRIPTION OF DRAWINGS

FIG. 4 is an exploded perspective view of the elements used in constructing the cloth covered stent;

FIG. 5 is a perspective view of the tissue ready to be placed on the cloth covered stent of FIG. 3;

FIG. 6 is a perspective view, partially in section, of the valve with portions removed;

Referring to FIG. 4, the valve includes a thin-walled stent 2 having an annular base 4 and three equally spaced upright posts 6 with scalloped upper edges 8 on the stent between posts 6. Throughout this application the term upper will be used for convenience to refer to the outflow end of the valve and lower will be used to refer to the inflow side, recognizing that the valve may not be upright where installed. Also, the term upper edge of the stent is used to include the side edges of the posts 6. Referring now to FIG. 1 the stent supports a tissue valve element 10 which surrounds the stent and has three cusps 12, 14, and 16 meeting along their upper edge portions in the closed position. The cusps are free to separate when the pressure below the valve exceeds that above to pass blood through the valve in a known manner. The flow of blood is from bottom to top in FIG. 1 along the axis 23 of the valve. Applicants refer to the article cited above in the application for a more complete description of the tissue and its assembly and operation.

Figure 1:
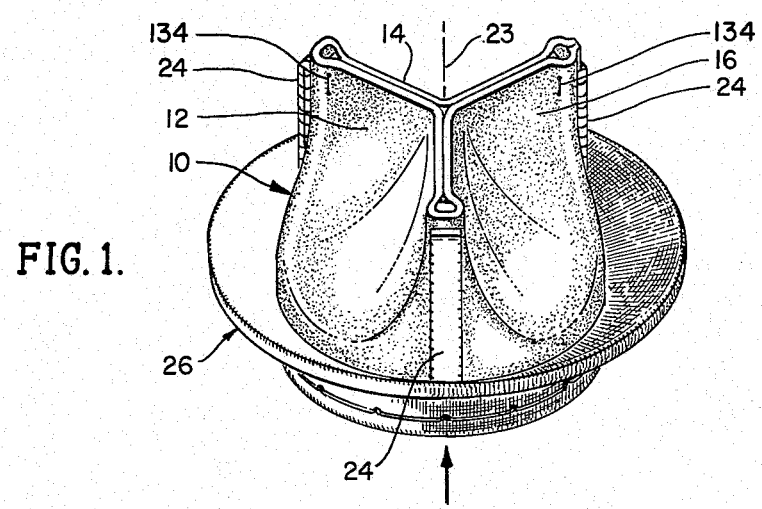
FIG. 1 is a perspective view of a completed valve.

A pledget and cover 24 extends down the outside of the tissue at each post, and a sewing ring or cuff 26 is provided for grafting the prosthetic valve into the heart valve annulus using well known surgical procedures.

Referring again to FIG. 4, the stent may be constructed of any of the known materials, suitable for cloth covered prosthetic heart valves, titanium or nickel-cobalt alloy or Teflon or Delvon plastic being among the alternatives available. Its bottom edge 28 preferably is slightly scalloped having its high points 30 beneath the posts 6. Each post 6 has sewing holes, 32, 34, and 36 three in the illustrated embodiment, spaced vertically near its upper end. Additional sewing holes 38, and 40 are spaced around the circumference of the base. In the illustrated embodiment the base 4 has one sewing hole 38 at the base of each post and five 40 between adjacent posts, but that number can be varied, as can the number on the posts.

The cloth covering preferably is of Dacron velour and includes an inner sleeve 42, a three piece outer sleeve 44, and three interior post sewing pads 46. The inner sleeve originally is of a cylindrical shape with scallops 48 removed as shown in FIG. 4, corresponding generally with the scallops 8 on the upper edge of the stent. The outside diameter of the inner sleeve is about the same as the inside diameter of the stent base 4. The outer sleeve pieces 44 can advantageously be cut from a cylinder of cloth to the shape shown, such that each has a post portion 50 with a rounded top 52 and two scalloped side edges 54, 56 and a base portion 58 with straight side edges 60, 62. The interior post pads 46 are each a short length of fabric of the same width as the posts 6 and having a rounded top 64.

Figure 8:
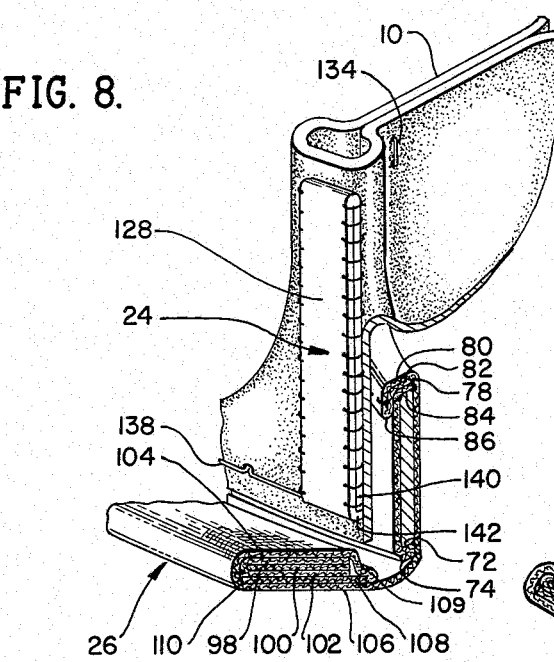
FIG. 8 is a perspective view, partially in section, of a portion of a partially completed valve.
Figure 9:
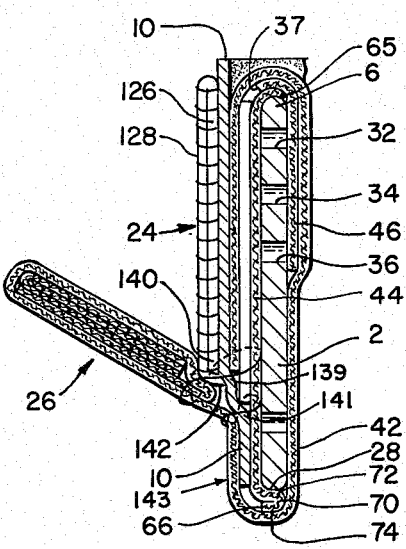
FIG. 9 is a sectional view, through the valve at a post of a completed valve.

Referring to FIGS. 8 and 9, three outer sleeve pieces 44 are each located on the outside of a respective stent post 6 and folded over the scalloped edges 8 and top of the stent post terminating at 78 flush with the inside surface of the stent. The three outer cloth pieces 44 do not cover the outside of the stent base 4 between the regions of the posts 6 as is evident from the spaces shown in FIG. 4, but extend to the seams 96 shown in FIG. 3. As best shown in FIG. 9, the bottom edge 66 of each outer sleeve piece is folded over the bottom edge 28 of the stent and then folded back at 70 to form a two layer 72, 74 pad at the bottom edge 28 and terminates at 66 about flush with the outer surface of the stent.

The three interior post sewing pads 46 are placed against the inner surfaces of the respective posts and cover the three post sewing holes 32, 34 and 36 terminating just below the bottom post hole 36. The upper end of each post pad is layered over the top of the post as shown at 37 in FIG. 9.

The inner sleeve 42 is located inside the stent and wrapped around the top edge 8 of the stent. This wrap in the post area is shown in FIG. 8 where it can be seen that the upper edge 78 of the inner sleeve is doubled back on itself and the double layer folded over the stent to provide two layers 80, 82 of inner sleeve of cloth in addition to the layer 84 of the outer sleeve cloth covering the edge of the post, with the top edge 78 of the inner cloth sleeve located just above that 65 of the outer sleeve. The doubled portion 86 of the inner sleeve also extends a short distance on the outside of the outer sleeve piece to provide extra padding over the outside of the posts over the sewing holes 32, 34 and 36 and the upper stent edge 8 where the tissue 10 is located.

FIG. 6 shows the arrangement of the cloth cover at the portions of the stent base 4 between the outer sleeve pieces 44. It can be seen that the inner sleeve does not terminate at the inner end of layer 82 in this area but is again folded back at 88 on itself to provide the third layer 90 of padding over the stent edge 8 and extends down to the outer face of the stent and is folded in double layers 92, 94 across the lower stent edge in the same manner as the outer sleeve pieces 72, 74 in FIG. 8. Thus, the inner sleeve 42 also serves the function of the outer sleeve at the base portions 4 between pieces of the outer sleeve 44.

Figure 3:
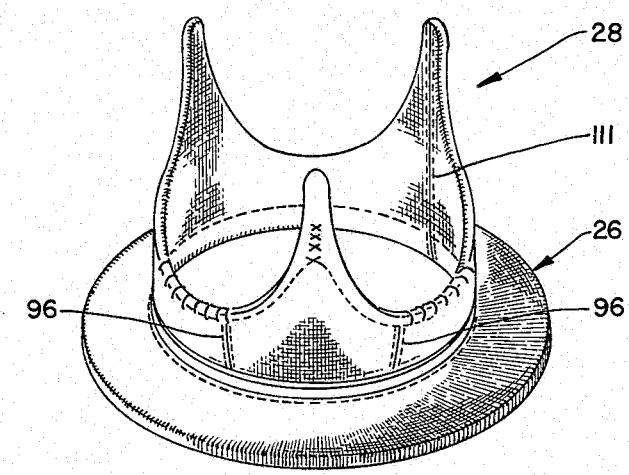
FIG. 3 is a perspective view of the stent covered with cloth and ready to receive the tissue, with the sewing ring turned down to show certain construction details.

The mating side edges of the outer sleeve portions and inner sleeve portions are all tucked in and sewn to each other in six seams 96 (FIG. 3). Appropriate other stitching of the cloth cover is also provided to hold the cloth in the described position covering the stent. Alternatively, the outer sleeve portions 44 can be made continuous around the stent using the arrangement of FIG. 7 all the way around instead of the arrangement of FIG. 6.

The bottom end of the inner cloth sleeve 42 extends a substantial distance below the bottom of the stent 2 and forms an integral annular sewing ring 26 for grafting the prosthetic valve to the heart.

Figure 2:
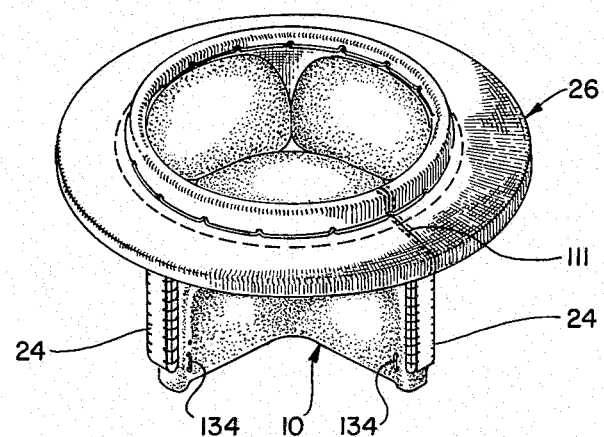
FIG. 2 is a perspective view of the same completed valve inverted.

As shown in FIG. 8, the sewing ring 26 is formed of an inner three layer 98, 100, 102 annular sewing pad 27, for example of woven Teflon or Dacron fabric, covered by the fabric of the inner sleeve 42 which is wrapped around the annular sewing pad 27 to provide one layer of cloth 104 above the pad 27 and two layers 106, 108 beneath the pad, and having its edge 110 covered by the layer of cloth 106. At the inner fold 109 between layers 104 and 108 a stitch is made to layer 106. As shown in FIGS. 2 and 3, a seam 111 was sewn in forming the inner sleeve portion into a cylinder. That seam 111 extends out into the sewing ring 26. When sewing the seam 111 the raw edges of cloth are tucked in so as not to be exposed.

Figure 7:
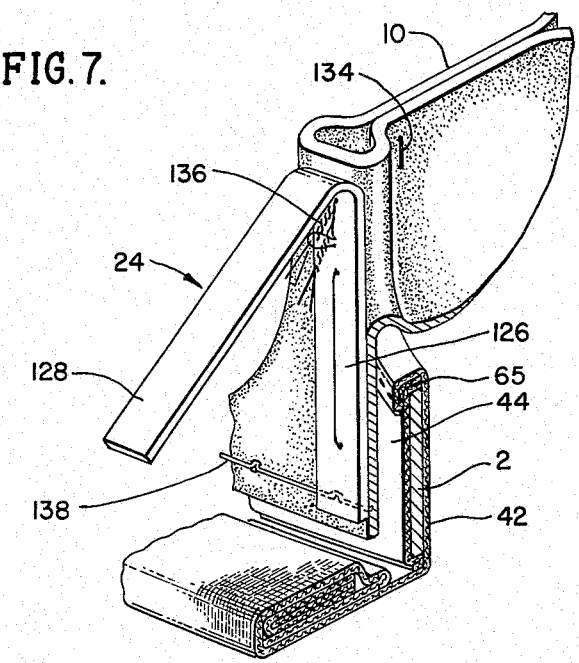
FIG. 7 is a perspective view, partially in section, of a portion of a partially assembled valve.

Referring now to FIG. 5, the tissue 10, in the exemplary embodiment bovine pericardium, is formed into a generally cylindrical shape of a diameter to fit over the cloth covered stent 28 as shown in FIG. 3. The top portion of the mating tissue edges 118, 120 are turned out face to face to form an overcast stitched seam 122 leaving the bottom portion of that seam 122 temporarily instiched. The tissue cylinder 10 is placed around the cloth covered stent 28 so as to circumscribe the base 4 and the posts 6 with the seam 122 centered on one post 6. A pledget and cover 24, as best shown in FIGS. 1 and 2, preferably of Teflon in a form not having fibers which can unravel, is located outside the tissue 10 at each post 6. Referring now to FIGS. 7 and 8, each pledget and cover has a sewing portion 126 which lays against the tissue and continues to a cover portion 128 which covers the stitches as will be described below. The tissue 10 and pledget 126 are attached to the stent using stitches through the upper holes 32, 34 and 36 in each post, and through the sewing portion 126 of the pledget. Small wedges 124, 130, and 132 are cut from the bottom portion of the tissue at the three posts 6 to provide relief to permit the tissue to close in cusps. The tissue valve is tucked around each individual post by stitches 134 as shown in FIG. 6. This causes the tissue valve to close in three cusps 12, 14 and 16 as shown in FIGS. 1 and 2. Each end 136, and 137 of the thread extends from the tuck stitch 134 through the inner sleeve, the inner post sewing pad, the upper hole in the stent, three layers of cloth in the outside of the post, the tissue outside the post, and the sewing portion of the pledget and are tied off as shown at 136 in FIG. 7. The pledget and cover 24 is not shown in FIG. 6 in order to more clearly show the other details.

The tissue is sewn to the cloth covered stent with stitches 138 through the holes 38, 40 in the base and the wedges 124, 130, and 132 are sewn together as darts, in each instance tying off the thread knots between the pledget cover 128 and the pledget sewing portion 126 at each post. The cover portion 128 of the pledget is folded down against, and stitched to, the sewing portion 126 to cover the knots. The sewing ring 26 is attached to the stent cover at two places 139 and 141 as shown in FIG. 9. Each set of stitches 139 and 141 continues all around the circumference of the sewing ring for solid attachment. It will be noted that the lower edges 140 and 142 of the pledget are covered by the sewing ring 26, but they extend down far enough only to barely be covered by the sewing ring but not far enough to add to the exterior diameter at the bottom edge of the stent.

Accordingly, it can be seen that this construction uses the pledget to cover all knots thereby eliminating any problems otherwise encountered from the hanging threads. The sewing ring is internal with the valve body cover to reduce risk of separation. All cut cloth edges of the Dacron cloth covering are covered by cloth leaving no exposed raw edges for possible unravelling. The bottom or inlet edge of the tissue also is covered. The only edges exposed are the side edges of the Teflon pledget and cover which are well out of the main blood flow and preferably are of a Teflon material which will not unravel, and the upper edges of the tissue which are pointed in the direction of flow.

Three layers of cloth padding are provided on both the bottom and top edges of the stent and also over the outside face of the stent near the top edge where the tissue wraps around the stent. Three layers of cloth also are provided between the tissue and the outside of each post in the area where the tissue is sewn to the post, and two layers are provided inside the post in that area. Those multiple layers provide padding between the tissue and the stent at the edge where the tissue might otherwise be damaged. Yet the ratio of inside diameter to outside diameter of the stent is very favorable because at the portion 143 which fits in the heart annulus, i.e. that portion beneath the sewing ring, there are only three layers of cloth plus the tissue and stent adding to the valve thickness. All of this as well as the other features expressed or inherent from the above discussion provide an improved valve construction well suited for commercial production.

What is claimed is:

1. A prosthetic heart valve comprising:
   a stent having an annular base and upright posts;
   tissue valve means circumscribing said stent posts;
   thread extending through said tissue stitching said tissue to said posts, said thread being twisted into knots outside the tissue;
   a first layer of fabric extending along each said post outside said tissue;
   said thread also stitching said first layer to said posts;
   a second layer of fabric covering said knots which are located between said first and second layers; and
   said first and second layers of fabric being a narrow pledget strip which is integral and continuous and folded back on itself over the knots.

2. A prosthetic heart valve in accordance with claim 1 and further comprising:
   cloth fabric covering said post between said post and said tissue.

3. A prosthetic heart valve in accordance with claim 1 wherein:
   said tissue is formed generally in a cylindrical shape circumscribing the posts of said stent as a group and is tacked around each individual post to form cusps for closing the valve passage.

4. A cloth covered stent for a prosthetic heart valve comprising:
   a stent having an annular base and plural upright posts;
   cloth fabric covering the interior surface of said stent;
   cloth fabric covering the exterior surface of said stent;
   a cylindrical tissue valve circumscribing said stent posts and said exterior cloth fabric;
   said interior fabric being tightly wrapped around the bottom edge of said stent covering the bottom edge of said exterior fabric, and preventing loose cloth at the bottom edge.

5. A cloth covered stent in accordance with claim 4 and further comprising:
   said interior fabric where wrapped around the bottom edge of said stent extending over the bottom edge of said tissue valve to cover said edge, and forming an integral annular sewing ring for grafting the stent onto a heart annulus.

6. A stent in accordance with claim 5 and said sewing ring further comprising:
   an annular fabric pad circumscribing the stent base;
   said interior fabric extending from its wrap around the bottom edge of the stent to wrap around the fabric pad and terminating in an edge adjacent said pad entirely covered by a layer of its own fabric.

7. A stent in accordance with claim 4 wherein:
   said bottom edge of the exterior fabric is doubled over the bottom edge of the stent to form two layers of cloth cover tight against said bottom edge in addition to the layer of the covering interior fabric.

8. A stent in accordance with claim 4 wherein:
   said interior and exterior fabrics are folded tightly over the top edge of said stent to form three layers of cloth covering over said edge.

9. A stent in accordance with claim 8 wherein:
   said fabric is folded over the outer surface of the stent adjacent its top edge to form three layers of cloth on said outer surface adjacent the top edge.

10. A stent in accordance with claim 4 wherein:
    at least partway around the stent the interior and exterior fabric are integral.

11. A stent in accordance with claim 4 wherein:
    said fabric is folded around the posts of said stent to form three layers of fabric on the outside of each post.

12. A stent in accordance with claim 4 and further comprising:
    a second layer of fabric on the interior of said posts.

13. A cloth covered stent for a prosthetic heart valve comprising:
    a thin-walled stent having an annular base and plural upright posts, said stent having upper and lower edges;
    a layer of cloth fabric covering the exterior surface of said stent;
    a cylindrical tissue valve circumscribing said stent and said exterior fabric;
    a layer of cloth fabric covering the interior surface of said stent;
    three layers of cloth fabric tightly wrapped over and covering the upper edge of said stent;
    three layers of cloth fabric tightly wrapped over and covering the lower edge of said stent;
    the bottom portion of the stent base which fits in the heart annulus having only one layer of cloth covering the interior and only two layers covering the exterior; and
    said fabric having no edges exposed.

14. A prosthetic heart valve comprising:
    a thin-walled, rigid stent having an annular base and three equally spaced upright posts extending axially from said base;
    the upper edge of said stent being scalloped in a smooth curve between said posts;
    the bottom edge of said stent being scalloped with the high points on the scallops beneath the respective posts;
    said stent base having a plurality of holes therethrough spaced around its circumference;
    each said stent post having a plurality of holes therethrough spaced along its length;
    three pieces of exterior Dacron velour fabric each covering the exterior of a post and of the base adjacent the post;
    each of said three pieces of exterior fabric being wrapped over the upper edge of the stent in a single layer and being folded over the bottom edge of the stent in a double layer;
    an interior Dacron velour fabric covering the interior surface of the stent;
    said interior fabric being folded over the top edge of the stent in a double layer where covered by the interior fabric;
    said interior fabric being folded over the top edge of the stent in a triple layer and also extending down to cover the exterior surface of the stent base where not covered by the exterior fabric and terminating in a double fold over the bottom edge of the stent base;
    the portion of the interior fabric folded over the upper edge of the stent also providing second and third layers of fabric on the exterior of the stent posts over the holes through the posts and along the outer surface of the stent adjacent its upper edge;

a fabric sewing pad between the interior surface of each post at the holes through the post and interior fabric;

a generally cylindrical valve element of bovine pericardium tissue circumscribing the stent and fabric cover;

stitches tacking the tissue around each post causing the tissue normally to close in three cusps;

a Teflon fabric pledget strip outside the tissue at each post, each said pledget strip including a first layer adjacent said tissue and a second layer outside first layer, said layers being integrally formed by a fold at the upper end and being stitched together along their long edges;

thread stitches attaching said tissue to said stent through the holes therethrough, all of said thread stitches being knotted between the two layers of said pledget;

the bottom of said interior fabric being wrapped over said double layer of fabric on the bottom edge of the stent and extending outward and upward to form an integral sewing ring;

the sewing ring having an annular three layered pad of Teflon fabric covered by two layers of the interior fabric on the underside and a single layer on the upper side, the edge of said inner fabric being on the inner layer of the two underside layers and covered by the outer layer of said two layers; and said sewing ring being sewn to said tissue and covering the bottom edges of the pledget.

* * * * *